United States Patent [19]
Campbell et al.

[11] Patent Number: 6,135,117
[45] Date of Patent: Oct. 24, 2000

[54] NON-OCULAR CIRCADIAN CLOCK RESETTING IN HUMANS

[75] Inventors: Scott S. Campbell, Chappaqua; Patricia J. Murphy, Ossining, both of N.Y.

[73] Assignee: Cornell Research Foundation, Inc., Ithaca, N.Y.

[21] Appl. No.: 09/074,455

[22] Filed: May 7, 1998

Related U.S. Application Data

[60] Provisional application No. 60/046,188, May 12, 1997, abandoned, and provisional application No. 60/072,121, Jan. 22, 1998, abandoned.

[51] Int. Cl.[7] ................................................. A61B 19/00
[52] U.S. Cl. ............................................. 128/898; 607/88
[58] Field of Search ............................... 128/898; 607/88

[56] References Cited

U.S. PATENT DOCUMENTS

| | | |
|---|---|---|
| 3,670,193 | 6/1972 | Thorington et al. . |
| 4,600,723 | 7/1986 | Short et al. . |
| 4,858,609 | 8/1989 | Cole . |
| 4,893,291 | 1/1990 | Bick et al. . |
| 5,000,752 | 3/1991 | Hoskin et al. . |
| 5,079,682 | 1/1992 | Roberts . |
| 5,086,770 | 2/1992 | Prangley . |
| 5,140,562 | 8/1992 | Moore-Ede et al. . |
| 5,163,426 | 11/1992 | Czeisler et al. . |
| 5,167,133 | 12/1992 | Schmidt . |
| 5,167,228 | 12/1992 | Czeisler et al. . |
| 5,169,380 | 12/1992 | Brennan . |
| 5,176,133 | 1/1993 | Czeisler et al. . |
| 5,197,941 | 3/1993 | Whitaker . |

(List continued on next page.)

FOREIGN PATENT DOCUMENTS

| | | |
|---|---|---|
| 0 469 227 A1 | 2/1992 | European Pat. Off. . |
| WO 95/25563 | 9/1995 | WIPO . |

OTHER PUBLICATIONS

L. E. Scheving et al., "The Persistence of a Circadian Rhythm in Histamine Response in Guinea Pigs Maintained Under Continuous Illumination", The Anotomical Record, vol. 175, No. 1, 1973, pp. 1–6.

P. Altmeyer et al., "Influence of Whole–Body UV Irradiation on Endocrinological Parameters", Dermatologica, vol. 166, 1983, pp. 186–191.

R. Woodhouse et al., "Responses of Albino and Hooded Rats to Various Illumination Choices in a Six–Chambered Alleyway", Perceptual and Motor Skills, vol. 61, 1985, pp. 343–354.

T. J. Savides et al., "Natural Light Exposure of Young Adults", Physiology & Behavior An International Journal, vol. 38, No. 4, 1986, pp. 571–574.

(List continued on next page.)

*Primary Examiner*—Vincent Millin
*Assistant Examiner*—Kelly O'Hara
*Attorney, Agent, or Firm*—Nixon Peabody LLP

[57] ABSTRACT

A method for resetting the phase of the human circadian clock and for enhancing alertness and performance in humans. The method involves the application of non-solar photic stimulation, in the range of 15 to 150,000 lux, to any non-ocular region of the human body during wakefulness or during sleep. Preferably, the photic stimulation has a wavelength within the visible spectrum (~400–750 nm). The method can be used to both delay and advance the circadian clock according to a phase response curve (PRC). The method may also be used for acute/immediate enhancement of alertness and performance. The method is applicable to alleviation of problems associated with "jet-lag", shift work sleep disturbance, and other sleep disturbances involving misalignment of circadian rhythms. The method provides a novel technique for shifting the phase of the circadian clock, and enhancing alertness and performance, using existing, or newly-developed devices.

44 Claims, 7 Drawing Sheets

U.S. PATENT DOCUMENTS

| | | |
|---|---|---|
| 5,242,941 | 9/1993 | Lewy et al. . |
| 5,259,380 | 11/1993 | Mendes et al. . |
| 5,292,345 | 3/1994 | Gerardo . |
| 5,300,097 | 4/1994 | Lerner et al. . |
| 5,327,331 | 7/1994 | Roberts . |
| 5,343,121 | 8/1994 | Terman et al. . |
| 5,358,503 | 10/1994 | Bertwell et al. . |
| 5,441,528 | 8/1995 | Chang et al. . |
| 5,447,528 | 9/1995 | Gerardo . |
| 5,503,637 | 4/1996 | Kyricos et al. . |
| 5,545,192 | 8/1996 | Czeisler et al. . |
| 5,562,719 | 10/1996 | Lopez-Claros . |
| 5,589,741 | 12/1996 | Terman et al. . |
| 5,648,656 | 7/1997 | Begemann et al. . |
| 5,716,978 | 2/1998 | Lewy et al. . |

OTHER PUBLICATIONS

C. A. Czeisler et al., "Bright Light Resets the Human Circadian Pacemaker Independent of the Timing of the Sleep–Wake Cycle", Science, vol. 233, 1986, pp. 667–671.

T. A. Wehr et al., "Eye Versus Skin Phototherapy of Seasonal Affective Disorder", American Journal of Psychiatry, vol. 144, No. 6, 1987, pp. 753–757.

C. A. Czeisler et al., "Bright Light Induction of Strong (Type 0) Resetting of the Human Circadian Pacemaker", Science, vol. 244, 1989, p. 1328.

E. Van Cauter et al., "Strategies for Resetting the Human Circadian Clock", The New England Journal of Medicine, vol. 322, No. 18, 1990, pp. 1306–1308.

A. T. Winfree, "Resetting the Human Clock", Nature International Weekly Journal of Science, vol. 350, No. 6313, 1991, p. 18.

B. Iyengar, "Melanocytes–A UV Sensitive Neural Network and Circadian Rhythms", Acta Anatomica, vol. 144, No. 4, 1992, pp. 332–335.

R. G. Foster, "Photoreceptors and Circadian System", American Psychological Society, vol. 2, No. 2, 1993, pp. 34–39.

B. Iyengar, "Indoleamines and the UV–Light–Sensitive Photoperiodic Responses of the Melanocyte Network: A Biological Calendar?" Experientia 50, 1994, pp. 733–736.

C. A. Czeisler et al., "Suppression of Melatonin Secretion in Some Blind Patients by Exposure to Bright Light", New England Journal of Medicine, vol. 332, No. 1, 1995, pp. 6–11.

D. A. Golombek et al., "Let There Be Light: Signal Transduction in a Mammalian Circadian System", Brazilian Journal of Medicine and Biological Research, vol. 29, No. 1, 1996, pp. 1–148.

A. E. Reinberg et al., "Synchronisation Et Dyschronisme Des Rythmes Circadiens Humains", Pathologie Biologie, vol. 44, No. 6, 1996, pp. 487–495.

S. Reuss, "Components and Connections of the Circadian Timing System in Mammals", Cell & Tissue Research, vol. 285, No. 3, 1996, pp. 353–378.

D.A. Oren, "Humoral Phototransduction Blood is a Messenger", The Neuroscientist, vol. 2, No. 4, 1996, pp. 207–210.

S. Campbell et al., "Extraocular Circadian Phototransduction in Humans", Submitted to Science Aug. 11, 1997, pp. 1–21.

PHASE ADVANCE = 2.43 h

NON-OCULAR CIRCADIAN CLOCK RESETTING IN HUMANS

This application claims the benefit of U.S. Provisional Application No. 60/046,188 filed May 12, 1997 now abandoned and U.S. Provisional Application No. 60/072,121 filed Jan. 22, 1998 now abandoned.

This invention was made with Government support under Grant No(s). R01MH45067 and K02MH01099, awarded by the National Institute of Health. The Government has certain rights in the inventions.

BACKGROUND OF THE INVENTION

1. Field of the Invention

This invention relates to a method for resetting the phase of the human circadian clock and for enhancing alertness and performance in humans by application of non-solar photic stimulation, in the range of 15 to 150,000 lux, to any non-ocular region of the human body.

2. Related Art

As with all vertebrates, humans exhibit temporal organization in behavior and in numerous physiological functions. In response to the natural alternation in light and dark, virtually all species have developed endogenous rhythms with frequencies close to 24 hours. These internally generated, self-sustaining rhythms are known as circadian rhythms (from the Latin circa =about, and dies =day). The pervasive nature of such rhythms suggests that circadian temporal organization is vital to the overall well-being of the organism. Numerous systems and functions are mediated by the circadian system including hormonal output, body temperature, rest and activity, sleep and wakefulness, and motor and cognitive performance. In all, literally hundreds of circadian rhythms in mammalian species have been identified.

Left to run at its inherent frequency, the human biological clock that is responsible for the generation of circadian rhythms exhibits a daily periodicity of slightly longer than 24 hours. Thus, a daily correction to the clock must be made for our internal rhythms to remain synchronized or 'entrained' to the natural 24 hour day. It is widely accepted that exposure to the natural light/dark cycle provides the strongest signal to entrain the human circadian system to the geophysical day. Inadequate exposure to light of sufficient intensity is a contributing factor in disorders associated with biological rhythm disturbance, such as seasonal affective disorder (SAD), jet lag from transmeridian travel, shift work and some types of insomnia (advanced and delayed sleep phase syndromes). Timed exposure to artificial bright light to the eyes has been used successfully to treat such disorders. Some examples of studies relating to the effects of timed ocular exposure to artificial bright light are discussed in U.S. Pat. Nos. 5,167,228 and 5,176,133 to Czeisler, which are herein incorporated by reference.

There is compelling evidence that bright ambient illumination on the eyes can have an immediate, acute enhancing effect on alertness and performance. By way of example, the article entitled, "Enhancement of Nighttime Alertness and Performance with Bright Ambient Light" by Scott S. Campbell and Drew Dawson in *Physiology & Behavior* Vol. 48, pp. 317–320, 1990, demonstrates that ocular exposure to illumination of about 1,000 lux enhances a human's alertness and performance. This non-circadian property of light exposure is of particular relevance to people who must work night or rotating shift work schedules, since declines in alertness and performance may result in increased accident rates, reduced productivity and increased health care costs.

It is widely accepted that the mammalian circadian clock which is located in the brain, within the suprachiasmatic nuclei (SCN) of the hypothalamus, receives photic information via the eyes, by visual and/or non-visual ocular pathways originating in the retina. It is also widely acknowledged that light acts to enhance alertness and performance via an ocular route(s). Yet, it has been recognized for decades that many species of birds and reptiles possess extra-ocular photoreceptors, and it has been demonstrated that circadian and photoperiodic response to light can be mediated entirely by such photoreceptors. In contrast, it is generally assumed that such nonvisual circadian photoreceptors in mammals reside within the retina, and that mammals do not possess the capacity for extraocular circadian photoreception. This conclusion is based on studies showing a failure of several rodent species to entrain to a light/dark cycle, or to respond to pulses of light with shifts in circadian phase, following complete optic enucleation.

Perhaps because of the widespread acceptance of the notion that mammals have no capacity for extraocular circadian photoreception, only two studies have examined whether extraocular light exposure can impact brain functioning in humans. In a study of blind subjects, Czeisler and coworkers found an absence of light-induced melatonin suppression during ocular shielding in two individuals who did show melatonin suppression when light fell on their eyes. A decade earlier, Wehr and coworkers reported a lack of clinical response in seasonal affective disorder when patients' skin (face, neck, arms and legs) was exposed to a bright light stimulus (2500 lux) while their eyes were shielded. No study has examined specifically whether circadian phase resetting can be achieved in humans via extraocular pathways.

As noted above, ocular exposure to timed bright light has been shown to be an effective remedy for circadian rhythm disorders. Unfortunately, treatment regimens involving ocular exposure to bright light are tedious and time-consuming. Many patients are simply unwilling or unable to remain relatively stationary for extended periods gazing at a bright light stimulus.

Additionally, the nature of the phase response curve to light dictates that the largest shifts, both advances and delays, are achieved at times during which people are typically asleep. Thus, all but the most committed users of bright light treatments fail to benefit from the most efficient temporal application of the intervention. Attempts have been made to remedy these problems by the development of 'light visors', which are devices worn like a cap that are intended to permit the user more freedom of movement while receiving light exposure. In practice, such devices are likely to be poorly received since they also direct light toward the eyes, and therefore, limit the visual field.

Also, as noted above, ocular light exposure has been demonstrated to improve alertness and performance. Unfortunately, as with circadian clock resetting, the use of ocular light in this capacity has considerable drawbacks. By way of example, the implementation of bright ambient light is likely to be impractical for use in typical industrial control room settings. Rapidly increasing utilization of computer technology for monitoring and controlling plant operations calls for ambient lighting conditions that take into consideration the effects of glare and contrast on computer displays.

In summary, because light must still enter through the eyes, unrestricted vision cannot be achieved, and mobility is limited. Simply, any device that successfully gets light to the eyes, is likely to interfere with normal activities. The result is reduced compliance and limited effectiveness of light treatment interventions as currently applied.

SUMMARY OF THE INVENTION

The present invention is a method for resetting the phase of the human circadian clock, or enhancing alertness and performance in humans, by application of non-solar photic stimulation, in the range of 15 to 150,000 lux, to any non-ocular region of the human body. Preferably, the non-solar photic stimulation is substantially, if not solely, applied to a non-ocular region or regions. While there is substantial evidence that the human circadian clock can be reset with light exposure to the eyes, this is the first demonstration that circadian clock resetting can be achieved via non-ocular phototransduction.

The present invention is premised on the unexpected result that substantially non-ocular presentation of appropriately timed light in humans can induce circadian clock resetting. Specifically, bright light transmitted through the skin, in a manner that rules out the possibility of ocular photoreception, results in significant clock resetting. A systematic relationship exists between the timing of the non-ocular light stimulus and the magnitude and direction of phase shifts, resulting in a phase response curve. This unexpected result also underlies another component of the present invention—that non-ocular light exposure enhances alertness and performance. That is, it is reasonable to conclude that non-ocular light exposure has the same physiological consequences as ocular exposure whether impacting on the biological clock, or on other brain areas involved in maintenance of optimal alertness and performance.

These methods provide a number of advantages over the way in which ocular light exposure is applied for the purposes of resetting the circadian clock and enhancing alertness and performance. For example, non-ocular light can be administered in much less obtrusive ways by not restricting vision and mobility; patients are not required to remain stationary and to stare at lights for extended periods. Likewise non-ocular light removes the inconvenience and potential hazards associated with glare and eye fatigue. Another advantage of the invention is that non-ocular light exposure can be used by individuals for whom ocular light exposure is contraindicated. This group includes, but is not restricted to, individuals with glaucoma, corneal pathology, progressive retinal disease and cataracts. In addition, it is clear that blind individuals, with no ocular light perception, could benefit considerably from non-ocular light treatments, since many of these individuals are unable to remain synchronized to the environmental light/dark cycle.

Perhaps the most important advantage of this invention is that it enables light treatments to be administered during sleep. The nature of the phase response curve to light in humans dictates that the largest shifts, both advances and delays, are achieved at times during which people are typically asleep. That is, phase delays occur when light is administered during the late subjective night (within a several-hour window prior to the daily minimum in body temperature), whereas phase advances are achieved when light exposure occurs during the early subjective morning (within a several-hour window following the daily minimum in body temperature). One advantage of the invention is that it permits delivery of non-ocular light near the temperature minimum without requiring wakefulness, thus insuring maximum phase shifting.

One embodiment of the invention is a method for resetting the human circadian clock, comprising the steps of exposing the popliteal region of an awake human subject to light at preselected times based on the human phase response curve to non-ocular light. The result is a rapid phase delay or advance with the intention of resetting the circadian clock to the desired new phase.

Another embodiment of the invention is a method for resetting the human circadian clock, comprising the steps of exposing any non-ocular region of an awake human subject to light at preselected times based on the human phase response curve to non-ocular light. The result is a rapid phase delay or advance with the intention of resetting the circadian clock to the desired new phase.

Another embodiment of the invention is a method for resetting the human circadian clock, comprising the steps of exposing the popliteal region of a sleeping human subject to light at preselected times based on the human phase response curve to non-ocular light presented during sleep. The result is a rapid phase delay or advance with the intention of resetting the circadian clock to the desired new phase.

Another embodiment of the invention is a method for resetting the human circadian clock, comprising the steps of exposing any non-ocular region of a sleeping human subject to light at preselected times based on the human phase response curve to non-ocular light presented during sleep. The result is a rapid phase delay or advance with the intention of resetting the circadian clock to the desired new phase.

Another embodiment of the invention is a method for enhancing alertness and/or performance, comprising the steps of exposing the popliteal region of an awake human subject to light at times when enhanced alertness and/or performance is desired. The result is an immediate and acute increase in subjective and physiological levels of alertness and performance.

Another embodiment of the invention is a method for enhancing alertness and/or performance, comprising the steps of exposing any non-ocular region of an awake human subject to light at times when enhanced alertness and/or performance is desired. The result is an immediate and acute increase in subjective and physiological levels of alertness and performance.

Another embodiment of the invention is an apparatus that can advantageously administer light to a non-ocular region of a human. The apparatus may be a stationary device such as a fiber optic phototherapy system, or it may be a portable device, such as a battery-powered light emitting diode (LED) array.

DETAILED DESCRIPTION OF THE INVENTION

Figure 1:
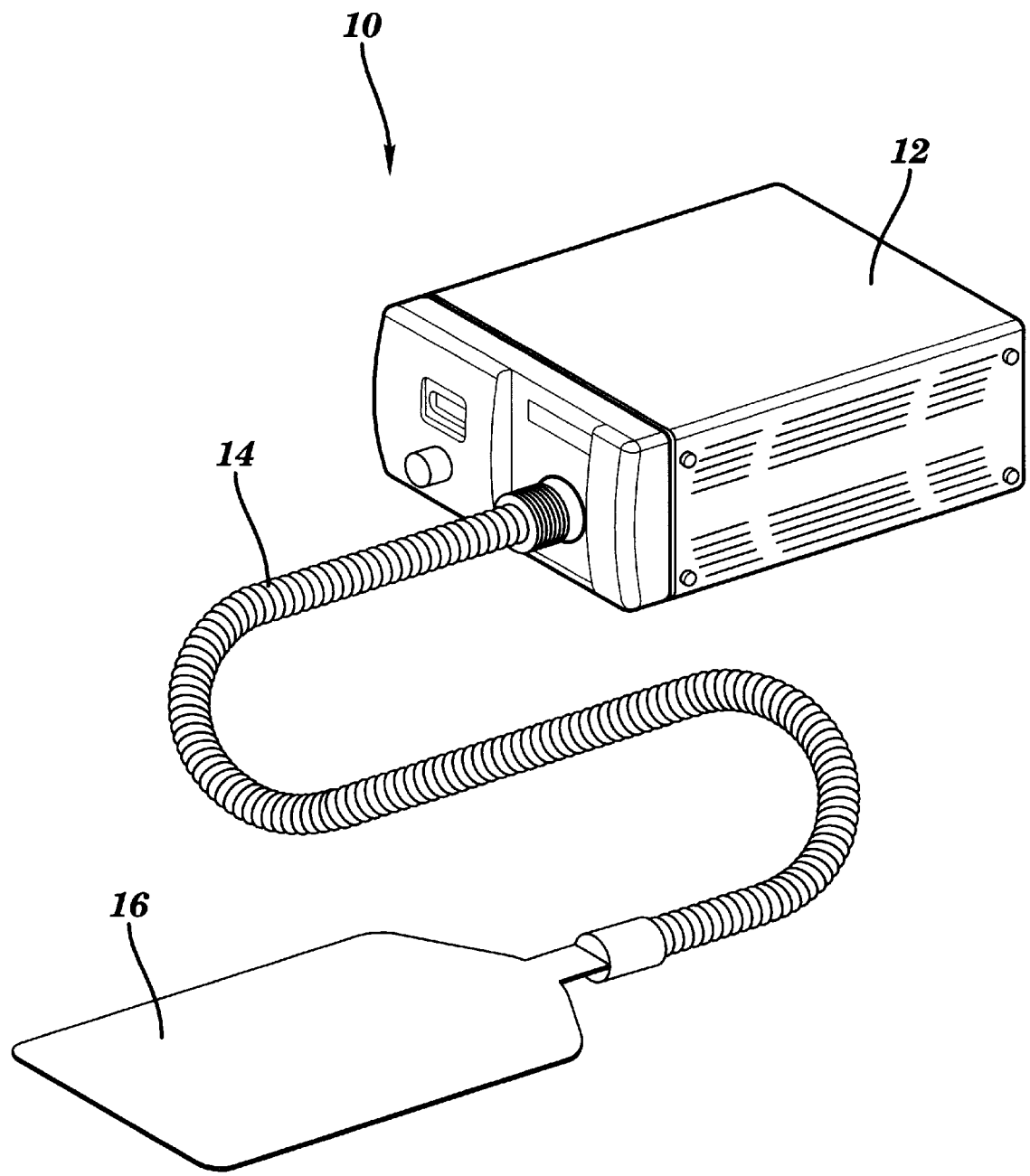
FIG. 1 is a perspective view of a device used to expose a non-ocular region of a human subject to light in order to reset the circadian clock or enhance alertness and/or performance, using the method in accordance with the present invention.

A method for resetting the phase of the human circadian clock and for enhancing alertness and performance in humans is disclosed. The method involves the application of non-solar photic stimulation to any non-ocular region of the human body. The preferred embodiment of the invention involves non-ocular exposure to light in a range from about 15 minutes to about 12 hours, and most preferably for a duration of 3 hours. Preferably the photic stimulation has an intensity in the range of 15 to 150,000 lux, and most preferably in a range from 10,000 to 13,000 lux. Preferably, the photic stimulation has a wavelength within the visible spectrum (~400–750 nm), and most preferably within the blue-green bandwidth (~455–540 nm). Preferably, the non-solar photic stimulation is substantially, if not solely, applied to a non-ocular region or regions. The method can be used on a sleeping human subject. The method can be used to both delay and advance the circadian clock according to a phase response curve (PRC). The method may also be used for acute/immediate enhancement of alertness and performance. The method is applicable to alleviation of problems associated with circadian rhythm sleep disorders, such as with "jet-lag" from transmeridian travel, shift work sleep disorder, advanced sleep phase syndrome, delayed sleep phase syndrome, non-24 hour sleep-wake disorder, irregular sleep-wake pattern, circadian rhythm disorders associated with blindness, circadian rhythm disorders in individuals for whom ocular light exposure is contraindicated, and other sleep disturbances involving misalignment of circadian rhythms. The method provides a novel technique for shifting the phase of the circadian clock, and enhancing alertness and performance, using existing, or newly-developed devices.

Empirical Basis for Clock Resetting With Non-Ocular Light Exposure

Circadian rhythms are endogenously generated oscillations of about twenty-four hours that provide temporal structure to a wide range of behavioral and physiological functions. Because the endogenous clock tends to run at a period close to, but not exactly 24 hours, a daily adjustment is required to synchronize, or entrain circadian rhythms to the external environment. The natural light/dark cycle is the most important signal for ensuring such entrainment, and many vertebrate and non-vertebrate species possess multiple photoreceptor systems through which circadian entrainment may be achieved. In the house sparrow, for example, three discrete input pathways for light to act on the circadian system have been identified. Similarly, a number of fish, amphibian and reptile species have extraocular and extrapineal pathways for circadian light transduction. Indeed, a host of species possess functional extraocular pathways for circadian entrainment by light, even in the presence of ocular photoreceptors that are capable of mediating the entraining influence of light.

In recent years, it has been suggested that the photoreceptors responsible for entraining the mammalian biological clock may not be the same cells that mediate vision. It has been shown, for example, that mice homozygous for the autosomal recessive allele rd ("retinally degenerate"), with no electrophysiological or behavioral visual responses to bright light, can be entrained to a light/dark cycle. Likewise, bright light exposure suppresses melatonin output in some totally blind human subjects, despite the fact that they have no conscious light perception and no pupillary light reflex. Such findings support the hypothesis that all vertebrates, including mammals, have specialized nonvisual photoreceptors that mediate circadian responses to the light-dark cycle. It is generally assumed, however, that such nonvisual circadian photoreceptors in mammals reside within the retina, and that mammals do not possess the capacity for extraocular circadian photoreception. This conclusion is based on studies showing a failure of several rodent species to entrain to a light/dark cycle, or to respond to pulses of light with shifts in circadian phase, following complete optic enucleation.

Perhaps because of the widespread acceptance of the notion that mammals have no capacity for extraocular circadian photoreception, only two studies have examined whether extraocular light exposure can impact brain functioning in humans. In their study of blind subjects, Czeisler and coworkers found an absence of light-induced melatonin suppression during ocular shielding in two of their subjects who did show melatonin suppression when light fell on their eyes. A decade earlier, Wehr and coworkers reported a lack of clinical response in seasonal affective disorder when patients' skin (face, neck, arms and legs) was exposed to a bright light stimulus (2500 lux) while their eyes were shielded. Detailed examination of the methods used in these studies makes it clear that they did not adequately test the ability of the human circadian timing system to respond to non-ocular light; in neither study was the output of the circadian clock actually measured. Likewise, there are problems of interpretation in most studies using non-human mammals. Furthermore, the comparative literature on circadian rhythms indicates that in a vast majority of instances, there is no fundamental difference in the manner in which mammalian and non-mammalian species respond to anipulations of the circadian clock. For these reasons, we decided to re-examine the issue of extraocular photoreception in humans.

Method for Non-Ocular Circadian Clock Resetting in Humans

Set forth below are some examples of using the method to reset the circadian clock in human subjects via a non-ocular pathway. The first two examples involve subjects who were awake during the non-ocular light exposure interval; the third example describes effects of non-ocular light exposure in sleeping subjects.

EXAMPLE 1

A total of 33 phase-shifting trials was carried out in 15 healthy subjects (mean age: 35.7 years; range: 22–67; 13 males, 2 females). Each laboratory session lasted for four consecutive days and nights, during which subjects were assigned randomly to either a control or an active condition. Successive laboratory visits were separated by at least 10 days. During the active sessions (phase delay, n=13; phase advance, n=11), light was presented at varying times relative to baseline circadian phase, in order to examine the response of the circadian clock throughout the 24-hour circadian cycle. A circadian cycle is one complete cycle of a circadian variable, such as body temperature. Under normal conditions a circadian cycle is about twenty-four hours. Light can be applied during one or more circadian cycles. The extraocular light stimulus in this example comprised a 3-hour pulse of light presented to the popliteal region, the area directly behind the knee joint.

In this particular example, the light source 10 was a BiliBlanket Plus (Ohmeda, Inc.), a fiber optic phototherapy device commonly used for home treatment of hyperbilirubinemia, as shown in FIG. 1. The light source 10 includes a halogen lamp (not shown) in a vented metal housing 12, which also contains a small fan to disperse heat generated by the lamp. Illumination from the halogen bulb leaves the housing 12 via 2400 optic fibers encased in a flexible plastic tube 14 about one meter (m) in length. The optic fibers terminate in a 4"×6" woven pad 16 approximately 0.25" thick. Because the light source 10 is remote, the fiber optic pad 16 generates no heat. The pad 16 was placed over the popliteal area of each leg which has ample surface vasculature and secured in place with a polyester athletic knee brace. During the a 3-hour light exposure interval, subjects remained seated in a reclining chair, with a table positioned over their laps.

To ensure that the light stimulus did not reach the retina, a 10'×10' black, opaque, double thickness polyester "skirt" was draped over the table, reaching the floor on all sides, and was secured with Velcro around the subject's waist. An exhaust fan (in addition to those in each BiliBlanket housing) was placed beneath the skirt to evacuate any heat produced by the halogen light source. The lamp housing 12 was placed beneath the table and under the skirt, so that any light escaping through the housing vents was obscured from the subject's eyes. Illumination at the subject's eye level never exceeded 20 lux. Accordingly, the illumination from light source 10 is substantially applied to a non-ocular region. Throughout their stay in the laboratory, when not sleeping and not involved in the experimental light manipulation, subjects were maintained in constant illumination of less than 50 lux.

Each light source 10 provided approximately 13,000 lux to the popliteal region in a bandwidth between approximately 455 and 540 nm. Although in this example one type of light source 10 operating within a particular bandwidth and at a particular intensity is disclosed, other types of light systems with other bandwidths and other intensities, such as broad-band white light provided by commercial fluorescent light boxes, may be used as needed or desired (see Example 2, below).

On the night prior to (night 1 in the lab) and the nights following the light stimulus (nights 3 and 4) subjects were required to remain in bed (and were allowed to sleep) from 2400 h until noon the following day. On the light exposure night (night 2 in the lab) sleep was necessarily displaced to accommodate presentation of the 3-hour light pulse. With the exception of this interval, subjects were in bed from 2400 h until noon on night 2, as well. Sleep was not permitted during the light exposure interval and continuous EEG and video monitoring of subjects throughout the exposure interval ensured compliance.

Body core temperature was recorded continuously. In a subset of sessions (n=18), hourly saliva samples were also collected for melatonin assay. Body core temperature was recorded in 2-minute epochs, using disposable rectal thermistors (Yellow Springs, Inc.) attached to MiniLogger ambulatory recording devices (Mini-Mitter, Inc., Sun River, Oreg). Saliva samples were collected under dim light from 1800 h until 2400 h on night 2 (prior to light exposure) and on night 4.

Melatonin levels were measured by radioimmunoassay (ALPCO, Inc., Windham, N.H.) using the Kennaway G280 antibody. All samples from a given subject during a given laboratory session were analyzed in the same assay. We have calculated an intraassay coefficient of variation of 2.1%; the inter-assay precision has been reported as 10.4%.

The nadir of the temperature rhythm and the dim light melatonin onset (DLMO) were used to evaluate circadian phase prior to and following presentation of the light pulse. The magnitude of phase shift achieved in each trial was determined by comparing subjects' baseline circadian phase (during the first 24 hours in the lab), with phase determined during the final 24 hours in the lab.

Figure 2A:
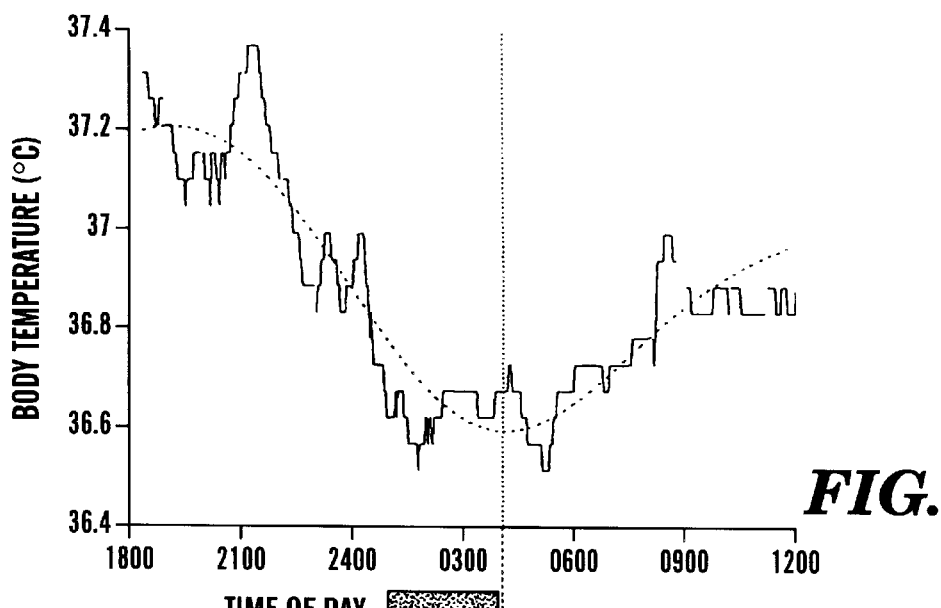
FIGS. 2A and 2B are graphs illustrating a delay in the circadian phase marker of minimum body temperature in one human subject induced using the method in accordance with the present invention.
Figure 2B:
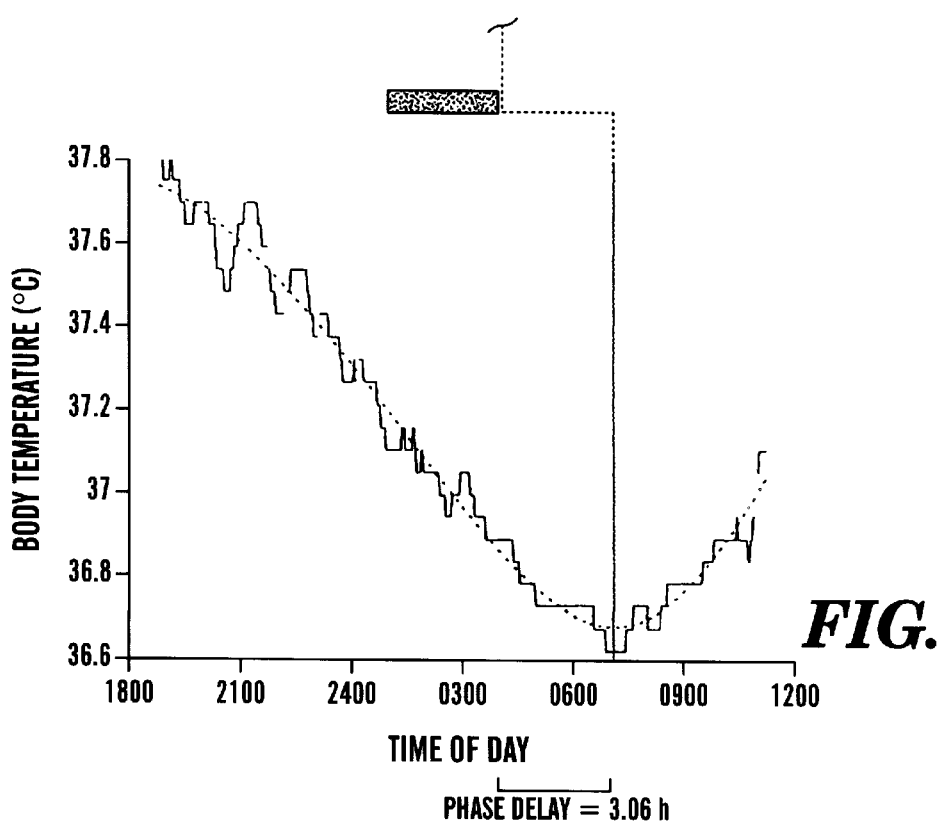

Referring to FIGS. 2A and 2B, an example of a delay in circadian phase in one subject in response to a 3-hour bright light presentation to the popliteal region is illustrated. Light was presented on one occasion between 0100 h and 0400 h on night 2 in the laboratory (black bar) while the subject (a 29 year-old male) remained awake and seated in a dimly lit room (ambient illumination<20 lux). Circadian phase was determined by fitting a complex cosine curve (dotted line) to the raw body core temperature data (solid line). Resulting phase estimates are indicated by vertical dotted lines. Baseline (night 1) circadian phase occurred at 0404 h as shown in FIG. 2A; circadian phase following light presentation (last 24 hours in the lab) occurred at 0708 h as shown in FIG. 2B. The phase angle between the mid-point of the light stimulus and the fitted body temperature minimum at baseline was 1.57 hours. The resulting phase delay was 3.06 hours.

Figure 3A:
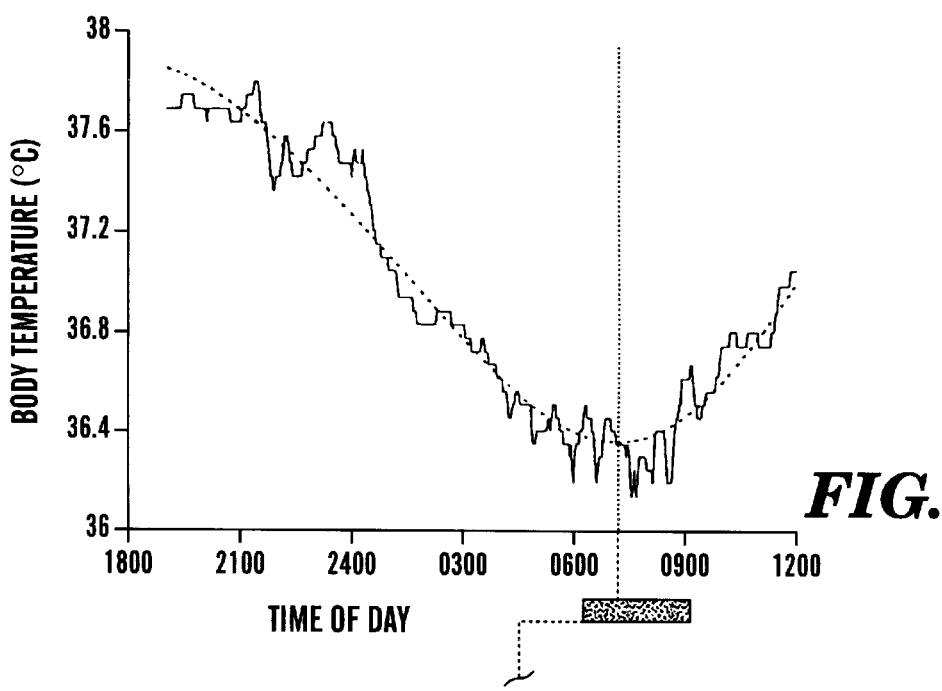
FIGS. 3A and 3B are graphs illustrating an advance in the circadian phase marker of minimum body temperature in one human subject induced using the method in accordance with the present invention.
Figure 3B:
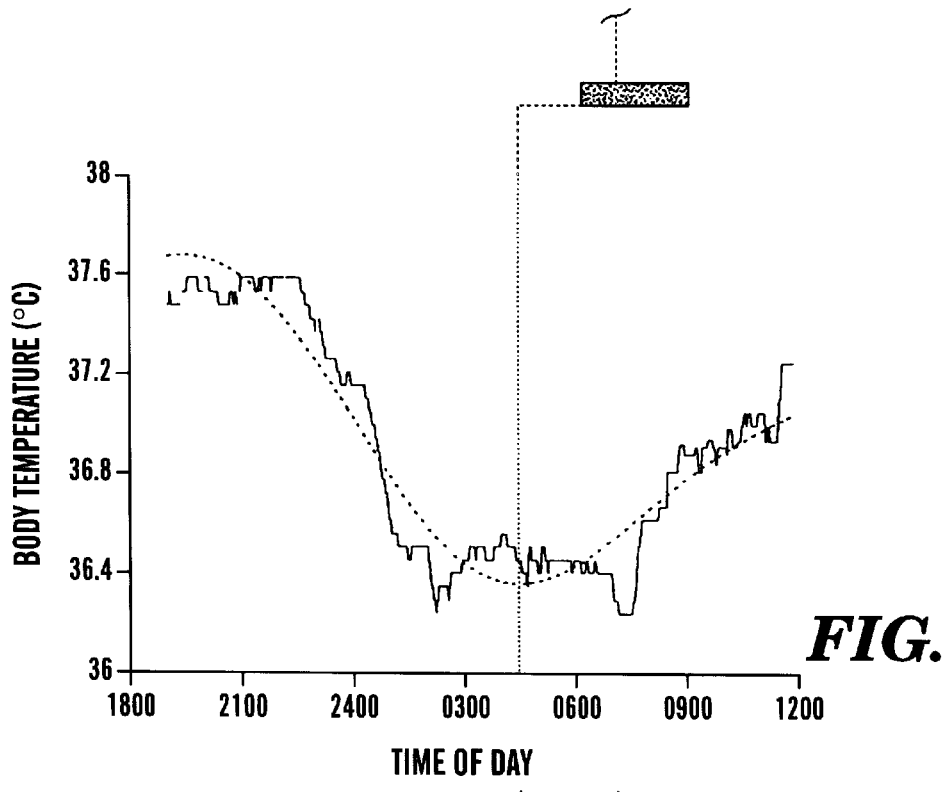

Referring to FIGS. 3A and 3B, an example of an advance in circadian phase in one subject in response to a 3-hour bright light presentation to the popliteal region is illustrated. Light was presented on one occasion between 0600 h and 0900 h, following night 2 in the laboratory (black bar) while the subject (a 44 year-old male) remained awake and seated in a dimly lit room (ambient illumination<20 lux). Circadian phase was determined by fitting a complex cosine curve (dotted line) to the raw body core temperature data (solid line). Resulting phase estimates are indicated by vertical dotted lines. Baseline (night 1) circadian phase occurred at 0713 h as shown in FIG. 3A; circadian phase following light presentation (last 24 hours in the lab) occurred at 0453 h as shown in FIG. 3B. The phase angle between the mid-point of the light stimulus and the fitted body temperature minimum at baseline was 0.28 h. The resulting phase advance was 2.34 hours.

Figure 4A:
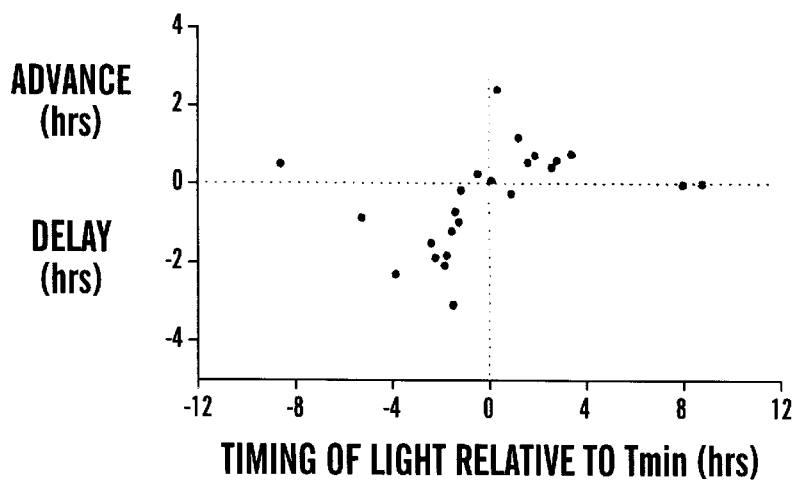
FIG. 4A is a graph illustrating the response of the endogenous circadian clock as measured by body temperature in a group of human subjects, induced by a single three-hour presentation of bright light to the popliteal region of subjects using the method in accordance with the present invention.

Response of the endogenous circadian pacemaker, as measured by body core temperature to a single 3-hour presentation of bright light to the popliteal region is illustrated in FIG. 4A. Each point represents the phase shift observed (advances are designated by positive numbers, delays by negative numbers on the y-axis) in response to bright light presented at a given time relative to the phase of body core temperature at baseline. "Timing of light relative to Tmin" (x-axis) refers to the interval between the midpoint of light presentation and the fitted temperature minimum. Magnitude of the observed phase shifts varied systematically as a function of this relationship, resulting in the generation of a classic phase response curve.

Figure 4B:
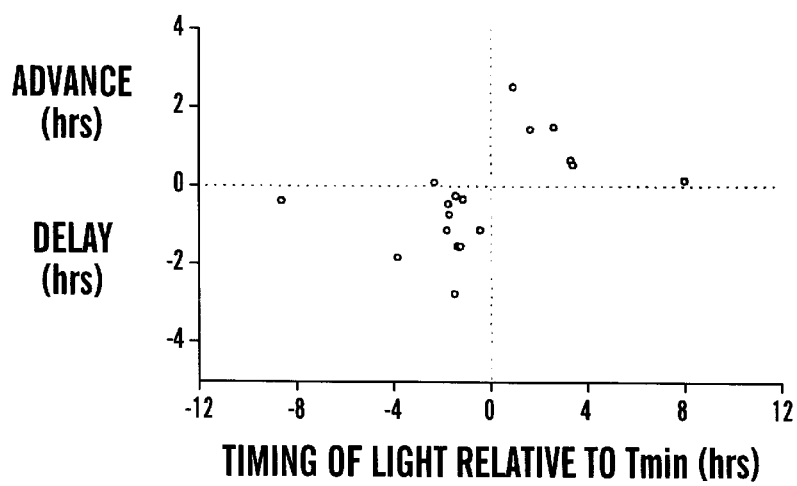
FIG. 4B is a graph illustrating the response of the endogenous circadian clock as measured by dim-light melatonin onset in a group of human subjects induced by a single three-hour presentation of bright light to the popliteal region of subjects using the method in accordance with the present invention.

In 18 of trials, the phase response of a second circadian marker, the onset of the endogenous melatonin rhythm under dim light conditions (DLMO) was assessed. The results of these assessments are shown in FIG. 4B. Each point represents the phase shift observed (advances are designated by positive numbers, delays by negative numbers on the y-axis) in response to bright light presented at a given time relative to the phase of body core temperature at baseline.

"Timing of light relative to Tmin" (x-axis) refers to the interval between the mid-point of light presentation and the fitted temperature minimum. As with body temperature, the timing of human subjects' nightly melatonin onset was shifted by the non-ocular light stimulus according to a phase response curve. The direction and magnitude of the shifts in DLMO were equivalent to those for temperature. Indeed, there was a significant correlation between the shift in body core temperature and the shift in melatonin onset (Spearman rank-order correlation: rho=0.704; P =0.009). The strong correlation between the two phase markers employed strongly suggests that the non-ocular light stimulus directly influenced the endogenous circadian clock and not simply the output variables.

Figure 4C:
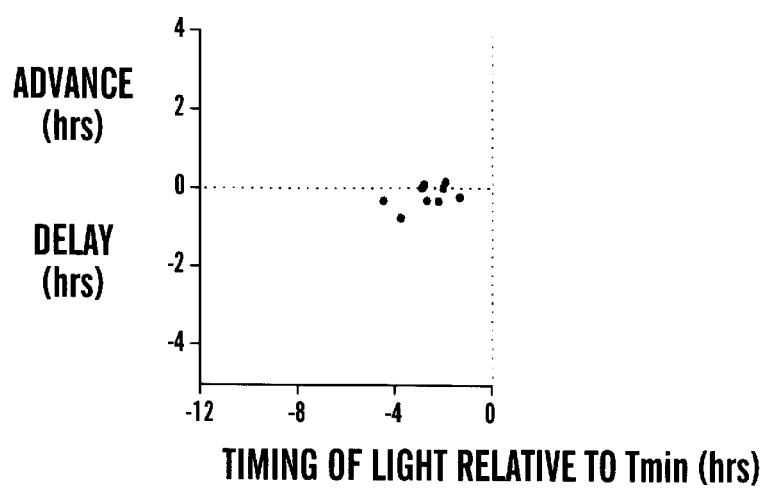
FIG. 4C is a graph illustrating the response of the endogenous circadian clock as measured by body temperature, in a group of human subjects, to a sham experimental condition (no light presented)

The phase shifts in the active sessions were the consequence of the light administration, and not systematically influenced by the experimental procedure itself. In the control condition, subjects underwent the identical protocol as in the delay condition, including application of the fiber optic pad and activation of the exhaust fans. However, in the control condition, the halogen bulb providing illumination to the optic pad was disconnected. Because in all conditions the light source was not turned on until they were seated and an opaque "skirt" was in place, subjects were unaware of whether light was actually being presented during a given session. Comparison of the phase of body temperature at baseline and following the control manipulation revealed no systematic phase shifts as a result of exposure to this protocol, as illustrated in FIG. 4C. Each point represents the change in phase following the control stimulus compared to baseline temperature phase. All no-light presentations occurred prior to baseline temperature minimum and therefore only that portion of the x-axis is shown.

Selection of the popliteal region for the site of light exposure in this study ensured (for methodological control) that light would not reach the retina. There is every reason to believe that timed light exposure presented to any non-ocular area of the body with adequate surface vasculature would result in similar circadian phase resetting.

EXAMPLE 2

In another example, six subjects (mean age 45.4 yrs; range, 30–71 yrs) were used to examine effects of non-ocular circadian clock resetting. As in Example 1, the popliteal region (the area directly behind the knee joint), was the site for the non-ocular light administration.

Illumination was provided by a light box (Apollo, Inc., Orem Utah) situated directly beneath the exposed knees (i.e. subjects wore short pants) of a subject sitting upright in a comfortable chair. At a distance of 18 inches, the light source provided about 10,000 lux illumination. The subjects' eyes were shielded from illumination by a blackout 'skirt' secured around the seated subject at the level of the rib cage, and extending to the floor surrounding the light. There was no other light source in the room besides the television situated 2 meters away from the subject and providing less than 5 lux at eye level. The bright light stimulus was presented from 2400 h to 0300 h.

Figure 5A:
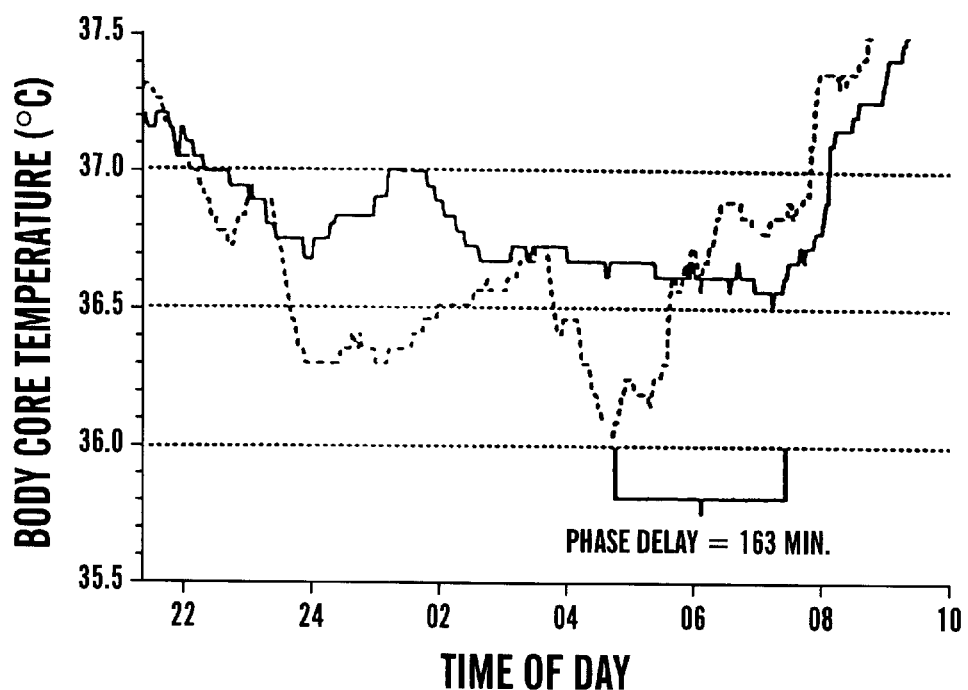
FIG. 5A is a graph illustrating nighttime temperature profiles of one human subject before (dotted line) and after (solid line) three hours of exposure to a 10,000 lux, broadband white light stimulus presented to the popliteal region between 2400 h and 0300 h on one occasion.

For the group, the average phase delay was 2.27 hrs in response to the non-ocular bright light stimulus. Four of the 5 subjects showed a delay, with phase-shifts ranged from 1.8 hrs to 4.7 hrs (one subject showed no phase-shift). FIG. 5A shows pre- and post-temperature plots obtained from one subject. The effects of the non-ocular light stimulus are apparent. This subject showed a clear phase-delay.

Figure 5B:
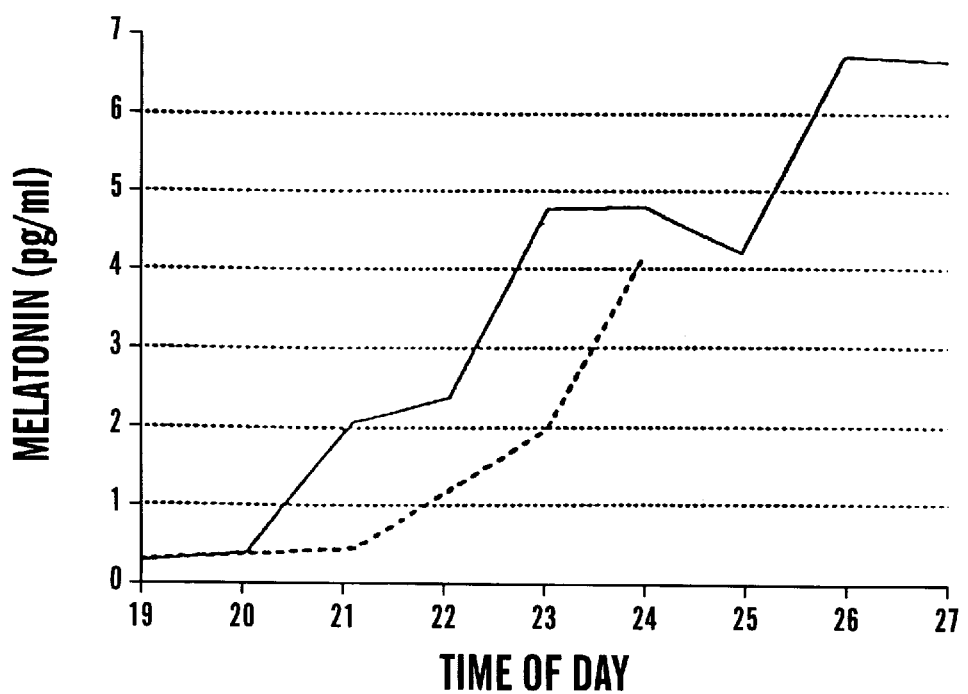
FIG. 5B is a graph illustrating nighttime melatonin onsets of one human subject before (dotted line) and after (solid line) three hours of exposure to a 10,000 lux, broad-band white light stimulus presented to the popliteal region between 2400 h and 0300 h on one occasion.

In this study, we also measured salivary melatonin levels collected each hour, beginning at 1800 h and continuing until subjects' bedtimes. Thus, on the light exposure night, samples were collected from 1800 h–0300 h; on the following day they were collected from 1800 h to 2400 h. Melatonin profiles from the same subject whose temperature is depicted in FIG. 5A, are shown in FIG. 5B. As with body temperature, nighttime melatonin onset showed a substantial phase-delay when measured on the evening following the 3-hr bright light stimulus to the popliteal region.

EXAMPLE 3

In another example, non-ocular light was administered to 10 subjects while they were asleep. As in Examples 1 and 2, the popliteal region (the area directly behind the knee joint), was the site for the non-ocular light administration. Each laboratory session lasted for four consecutive days and nights. Light was presented at varying times relative to baseline circadian phase, in order to examine phase response throughout the circadian cycle. The extraocular light stimulus consisted of a pulse of light presented to the popliteal region while subjects were sleeping. Subjects were asleep during the non-ocular light presentation as verified by conventional sleep laboratory techniques (electroencephalography). The magnitude of phase shift achieved in each trial was determined by comparing subjects' baseline circadian phase (during the first 24 hours in the lab), with phase determined during the final 24 hours in the lab.

Figure 6A:
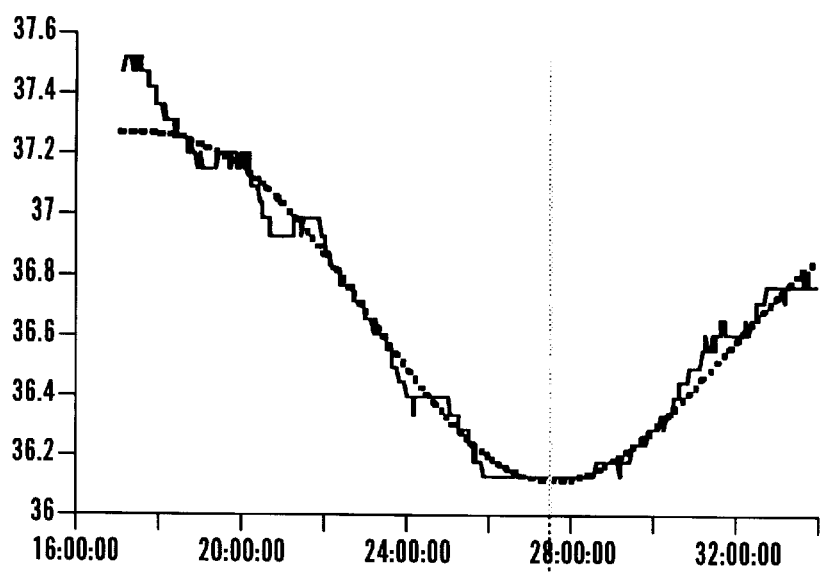
FIGS. 6A and 6B are graphs illustrating a delay in the circadian phase marker of minimum body temperature in one sleeping human subject induced using the method in accordance with the present invention.
Figure 6B:
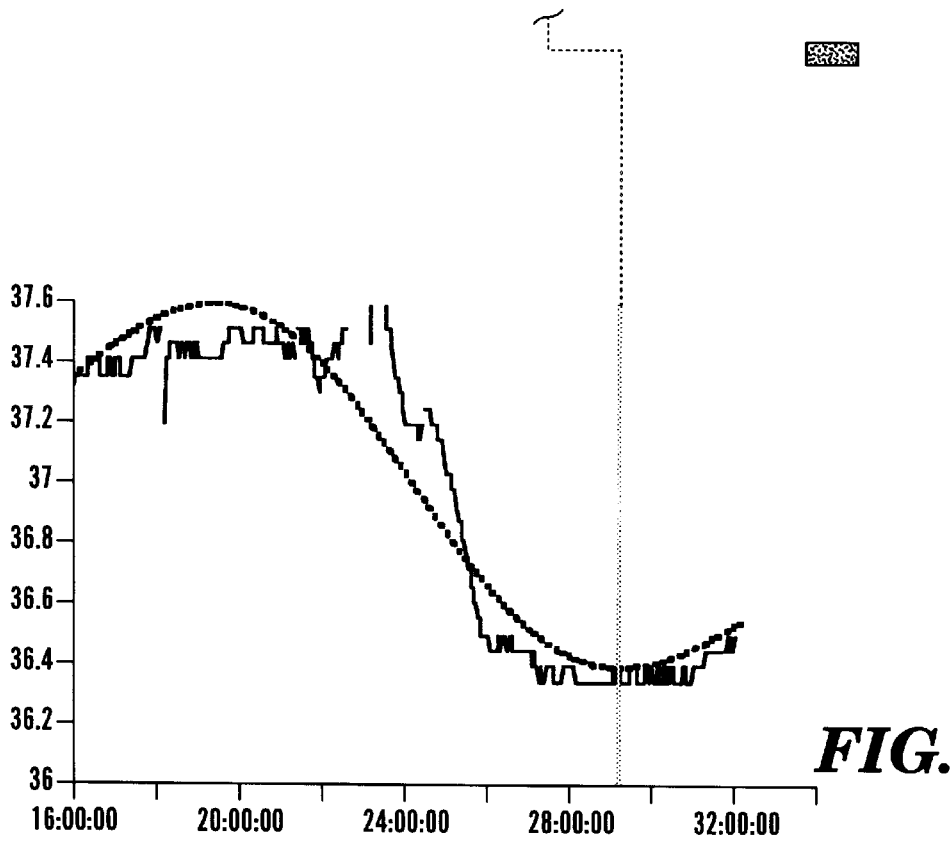

Referring to FIGS. 6A and 6B, an example of a delay in circadian phase in one subject (a 24 year-old male) in response to a 1.25-hour bright light presentation to the popliteal region during sleep is illustrated. Light was presented on two consecutive days between 0930 h and 1045 h (black bar) in a darkened room. Circadian phase was determined by fitting a complex cosine curve (dotted line) to the raw body core temperature data (solid line). Resulting phase estimates are indicated by vertical dotted lines. Baseline (night 1) circadian phase occurred at 0336 h as shown in FIG. 6A; circadian phase following light presentation (last 24 hours in the lab) occurred at 0517 h as shown in FIG. 6B.

The phase angle between the mid-point of the light stimulus and the fitted body temperature minimum at baseline was 6.52 hours (i.e., light was presented following the temperature minimum). The resulting phase delay was 1.68 hours. There was a corresponding delay in the onset of the melatonin rhythm (DLMO) of 1.87 hours.

Figure 7A:
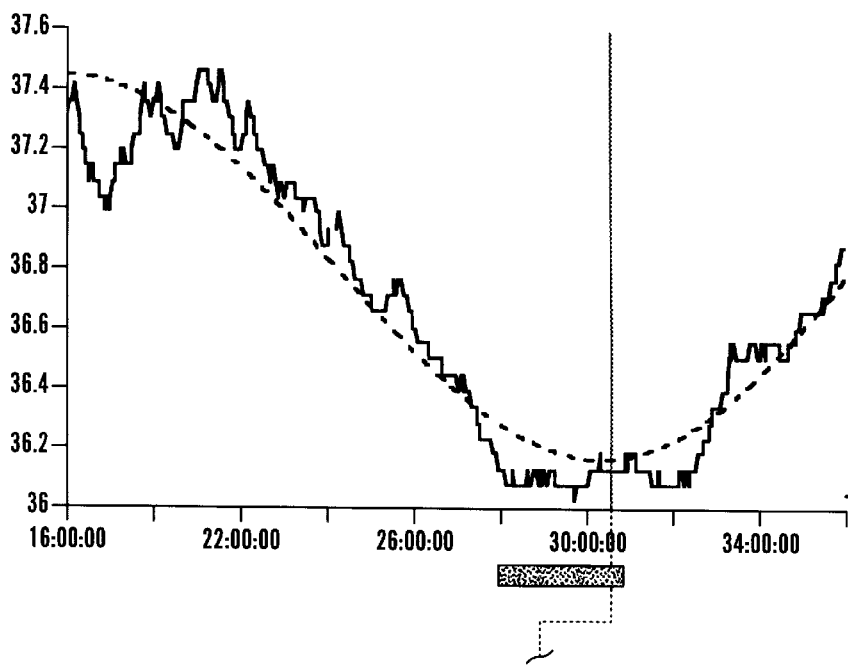
FIGS. 7A and 7B are graphs illustrating an advance in the circadian phase marker of minimum body temperature in one sleeping human subject induced using the method in accordance with the present invention.
Figure 7B:
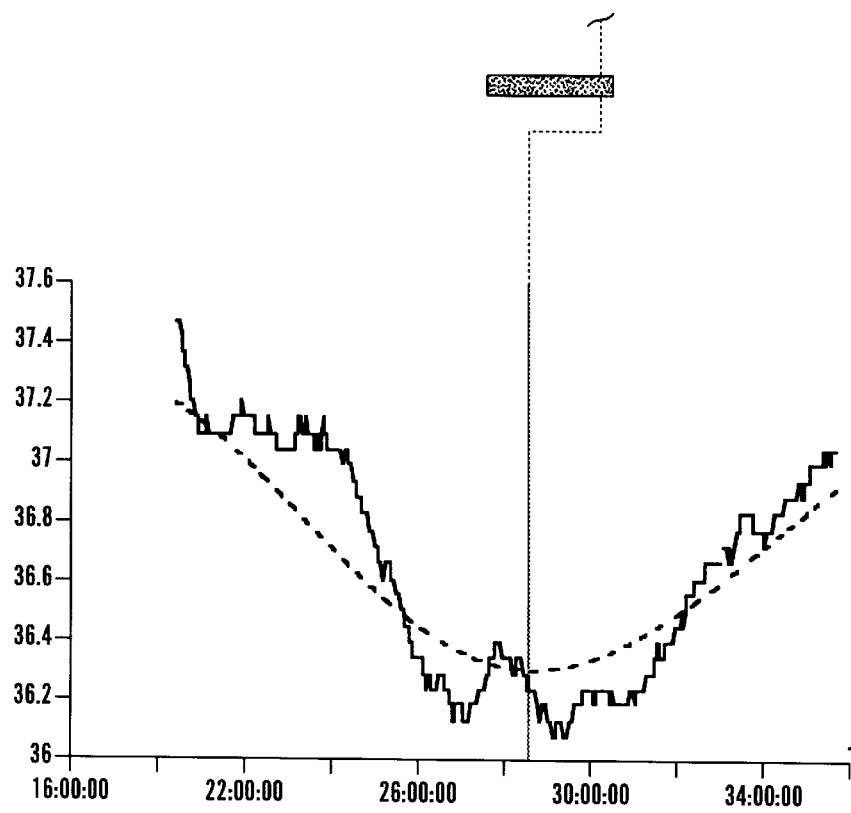

Referring to FIGS. 7A and 7B, an example of an advance in circadian phase in one subject (a 54 year-old male) in response to a 3-hour bright light presentation to the popliteal region during sleep is illustrated. Light was presented on two consecutive nights between 0400 h and 0700 h, (black bar) in a darkened room. Circadian phase was determined by fitting a complex cosine curve (dotted line) to the raw body core temperature data (solid line). Resulting phase estimates are indicated by vertical dotted lines. Baseline (night 1) circadian phase occurred at 0725 h as shown in FIG. 7A; circadian phase following light presentation (last 24 hours in the lab) occurred at 0545 h as shown in FIG. 7B. The phase angle between the mid-point of the light stimulus and the fitted body temperature minimum at baseline was −1.92 h (i.e., light was presented prior to the temperature minimum). The resulting phase advance was 1.67 hours.

EXAMPLE 4

Ocular exposure to light results in increased brain electrical activity. When EEG data are collected during ocular light exposure, then subjected to spectral analysis (Fast Fourier Transform method), power density in the higher frequency ranges (beta frequency band, approximately 21–32 Hz) is enhanced relative to EEG activity during dim light exposure. This increase in beta activity is indicative of higher levels of alertness, and has been associated with increased levels of psychomotor and cognitive performance. It is reasonable to assume that in the same manner as non-ocular exposure results in phase shifts similar to those achieved with ocular light pulses, non-ocular light exposure will also affect EEG beta activity in a manner similar to ocular exposure. The following example describes a pilot study that was undertaken to determine whether non-ocular light exposure resulted in acute increases in brain electrical activity.

Multiple samples of waking EEG data from one subject were collected during exposure of the popliteal region to a non-ocular light source, and during a control condition. In the control condition, electrical power was provided to the light source, but the halogen lamp providing illumination to the fiber optic cables was unplugged. The subject (a 25-year-old female) was seated in a dimly lit (<20 lux) room, with a double-thickness, black polyester 'skirt' fastened with Velcro around her waist. Two Biliblanket phototherapy devices were attached to the popliteal region of each leg as described earlier in Example 1. The devices were placed underneath the 'skirt' and behind the chair in which the subject was seated. The halogen lamp was unplugged or plugged in by the experimenter out of view of the subject. The black skirt ensured that the subject was not aware of whether the light source was activated or deactivated. The subject was instructed as follows: "Sit as still as possible, with your feet on the floor and arms at your side. Avoid any head or body movements and keep your eyes closed. We will inform you when you may open your eyes." Two EEG sites (C3 and 01) were referenced to linked mastoids; impedances for all were below 2kΩ Three minute intervals of EEG data were collected and digitized at a rate of 256 samples per second. The three minute samples were collected in the following order:

A) Eyes closed, light source activated.
B) Eyes closed, light source deactivated.
C) Eyes closed, light source deactivated.
D) Eyes closed, light source activated.

The average of the data from conditions A+D (light source 'on') and B+C (light source 'off') were used to investigate the effects of non-ocular light on EEG activity. After removal of visually detected eyeblink and muscle artifact, the data set from each of the conditions were subjected to spectral analysis (FFT), yielding the average power density ($\mu V^2$), in 2-second epochs. Both absolute and relative power density in predefined frequency bands (delta=1.5 4 Hz, theta=4–7 Hz, alpha=8–13 Hz, beta1=13–20 Hz, beta2=21–32 Hz) were calculated.

Total absolute power was higher when the non-ocular light source was activated relative to the control condition (15.4 vs. 10.6_$V^2$ for site C3; 11.8 vs 6.6_$V^2$ for site 01). Relative power in the alpha (16.1 vs 17.2 for site C3; 23.9 vs 24.0 for site 01) and theta (15.1 vs 15.2 for site C3; 11.5 vs. 10.4 for site 01) frequency bands did not differ between lights on and lights off conditions. However, delta power was substantially lower (24.0 vs. 31.6, while activity in both the low and high beta frequency bands was higher (23.5 vs. 17.4 for B1 at site C3; 23.7 vs. 19.6 for B1 at site 01; 22.7 vs. 18.0 for B2 at site C3; 27.0 vs. 22.2 for B2 at site 01) when the lights were activated.

These preliminary results indicate that non-ocular light exposure, even when the eyes are completed shielded from the light stimulus, may result in EEG activation at frequencies associated with higher alertness.

Devices for Facilitating the Method

The method described herein requires that a human subject be exposed to a non-ocular light source under conditions sufficient to reset the human circadian clock, or to acutely enhance alertness and performance. The device originally used to reduce the method to practice, as described in the examples above, can be altered in a number of ways to facilitate various applications of the method. The invention envisions several different means by which the light may be transmitted, including fiber optic configurations, light emitting diode (LED) arrays, bioluminescent derivations, and incandescent and fluorescent light sources.

The invention envisions the use of these various light sources designed to facilitate light exposure to a wide range of non-ocular sites. For example, a device is envisioned by which the foot or hand is covered (like a sock or glove), thereby exposing the entire area to illumination; another device is one by which the tympanic membrane is illuminated by LEDs incorporated in headphones or earplugs; another device is one by which the midriff is exposed to light by an illuminated wrap; another device is envisioned in which the source of illumination is not worn by the subject but illuminates a non-ocular site, for example, partially-illuminated bed linens.

Energy to operate the aforementioned devices may be provided by a variety of power sources that would enable the devices to be stationary or portable, for example a standard AC outlet or a battery.

We have described a variety of specific embodiments of the invention, but the method and device are not limited to these embodiments. The claims set forth below incorporate the full scope and definition of the invention.

What is claimed is:

1. A method of resetting a human circadian clock comprising the step of exposing a non-ocular region of a human subject to a non-solar photic stimulation during one or more circadian cycles to reset the human circadian clock.

2. The method according to claim 1 further comprising the step of assessing a time when a daily minimum body temperature for the human subject occurs, wherein said step of exposing the non-ocular region begins at an exposure time dependent upon the assessed time.

3. The method according to claim 2 wherein said step of exposing the non-ocular region begins before the assessed time.

4. The method according to claim 3 wherein said step of exposing the non-ocular region begins within about six hours prior to the assessed time.

5. The method according to claim 2 wherein said step of exposing the non-ocular region begins after the assessed time.

6. The method according to claim 5 wherein said step of exposing the non-ocular region begins within six hours after the assessed time.

7. The method according to claim 1 wherein said step of exposing the non-ocular region occurs while the human subject is awake.

8. The method according to claim 1 wherein said step of exposing the non-ocular region occurs while the human subject is asleep.

9. The method according to claim 1 wherein said step of exposing the non-ocular region lasts for a duration ranging from between about 15 minutes to about 12 hours.

10. The method according to claim 9 wherein the duration of said non-ocular exposure is about three hours.

11. The method according to claim 1 wherein said non-solar photic stimulation has an intensity between about 15 lux to about 150,000 lux.

12. The method according to claim 1 wherein said non-solar photic stimulation has an intensity between about 10,000 lux to about 13,000 lux.

13. The method according to claim 1 wherein said non-solar photic stimulation has a bandwidth in the visible spectrum.

14. The method according to claim 13 wherein said non-solar photic stimulation has a bandwidth between about 455 nanometers (nm) and 540 nm.

15. The method according to claim 1 wherein the given number of circadian cycles is one.

16. The method according to claim 1 wherein the given number of circadian cycles is two or more.

17. The method according to claim 1 wherein the non-ocular region of the human subject has ample surface vasculature.

18. The method according to claim 17 wherein the non-ocular region is a popliteal region of the human subject.

19. The method according to claim 1 wherein said step of exposing the non-ocular region is used to treat a circadian rhythm sleep disorder.

20. The method according to claim 19 wherein said step of exposing the non-ocular region is used to treat the circadian rhythm sleep disorder resulting from transmeridian travel (jet-lag).

21. The method according to claim 19 wherein said step of exposing the non-ocular region is used to treat Shift Work Sleep Disorder.

22. The method according to claim 19 wherein said step of exposing the non-ocular region is used to treat Advanced Sleep Phase Syndrome (ASPS).

23. The method according to claim 19 wherein said step of exposing the non-ocular region is used to treat Delayed Sleep Phase Syndrome (DSPS).

24. The method according to claim 19 wherein said step of exposing the non-ocular region is used to treat Non-24-Hour Sleep-Wake Disorder.

25. The method according to claim 19 wherein said step of exposing the non-ocular region is used to treat Irregular Sleep-Wake Pattern.

26. The method according to claim 1 wherein said step of exposing the non-ocular region is used to treat sleep and circadian rhythm disorders associated with blindness.

27. The method according to claim 1 wherein said step of exposing the non-ocular region is used to treat sleep and circadian rhythm disorders in individuals for whom ocular light exposure is contraindicated.

28. A method of resetting a human circadian clock comorising the steps of:

assessing a time when a minimum body temperature for a human subject occurs; and exposing a substantially non-ocular region of the human subject to a non-solar photic stimulation for one or more circadian cycles to reset the human circadian clock at an exposure time dependent upon the assessed time.

29. The method according to claim 28 wherein said step of exposing the non-ocular region begins before the assessed time.

30. The method according to claim 28 wherein said step of exposing the non-ocular region begins about six hours prior to the assessed time.

31. The method according to claim 28 wherein said step of exposing the non-ocular region begins after the assessed time.

32. The method according to claim 31 wherein said step of exposing the non-ocular region begins within six hours after the assessed time.

33. The method according to claim 28 wherein said step of exposing the non-ocular region occurs while the human subject is awake.

34. The method according to claim 28 wherein said step of exposing the non-ocular region occurs while the human subject is asleep.

35. The method according to claim 28 wherein said step of exposing the non-ocular region lasts for a duration ranging from between about 15 minutes to about 12 hours.

36. The method according to claim 35 wherein the duration of said non-ocular exposure is about three hours.

37. The method according to claim 28 wherein said non-solar photic stimulation has an intensity between about 15 lux to about 150,000 lux.

38. The method according to claim 37 wherein said non-solar photic stimulation has an intensity between about 10,000 lux to about 13,000 lux.

39. The method according to claim 28 wherein said non-solar photic stimulation has a bandwidth in the visible spectrum.

40. The method according to claim 39 wherein said non-solar photic stimulation has a bandwidth between about 455 nm and 540 nm.

41. The method according to claim 28 wherein the number of circadian cycles is one.

42. The method according to claim 28 wherein the number of circadian cycles is two or more.

43. The method according to claim 28 wherein the non-ocular region of the human subject has ample surface vasculature.

44. The method according to claim 43 wherein the non-ocular region is a popliteal region of the human subject.

* * * * *